(12) United States Patent
Kanda

(10) Patent No.: US 12,366,513 B2
(45) Date of Patent: Jul. 22, 2025

(54) SAMPLE OBSERVATION APPARATUS

(71) Applicant: KYOCERA Corporation, Kyoto (JP)

(72) Inventor: Eiji Kanda, Yasu (JP)

(73) Assignee: KYOCERA CORPORATION, Kyoto (JP)

( * ) Notice: Subject to any disclaimer, the term of this patent is extended or adjusted under 35 U.S.C. 154(b) by 183 days.

(21) Appl. No.: 18/018,843

(22) PCT Filed: Jul. 14, 2021

(86) PCT No.: PCT/JP2021/026509
§ 371 (c)(1),
(2) Date: Jan. 30, 2023

(87) PCT Pub. No.: WO2022/024768
PCT Pub. Date: Feb. 3, 2022

(65) Prior Publication Data
US 2023/0349806 A1    Nov. 2, 2023

(30) Foreign Application Priority Data

Jul. 31, 2020 (JP) .................................. 2020-130736

(51) Int. Cl.
*G01N 15/0205* (2024.01)
*G01N 15/075* (2024.01)
(Continued)

(52) U.S. Cl.
CPC ....... *G01N 15/0211* (2013.01); *G01N 15/075* (2024.01); *G01N 21/51* (2013.01); *G02B 21/06* (2013.01)

(58) Field of Classification Search
CPC .. G01N 15/0211; G01N 15/06; G01N 15/075; G01N 15/1436; G01N 2021/0112;
(Continued)

(56) References Cited

U.S. PATENT DOCUMENTS 8,101,912 B2 * 1/2012 Yamaguchi ........ G06V 40/1312
250/370.08
2009/0134328 A1   5/2009 Yamaguchi et al.
(Continued)

FOREIGN PATENT DOCUMENTS

JP    2009-129365 A    6/2009
JP    2010-88665 A    4/2010
(Continued)

OTHER PUBLICATIONS

Bruder, S., Reifenrath, M., Thomik, T et al. Parallelised online biomass monitoring in shake flasks enables efficient strain and carbon source dependent growth characterisation of *Saccharomyces cerevisiae*. Microb Cell Fact 15, 127 (2016). https://doi.org/10.1186/s12934-016-0526-3 (Year: 2016).*

(Continued)

*Primary Examiner* — Kara E. Geisel
*Assistant Examiner* — Jonathon Cook
(74) *Attorney, Agent, or Firm* — Procopio, Cory, Hargreaves & Savitch LLP

(57) ABSTRACT

A sample observation apparatus includes a transparent vessel that accommodates a medium containing a sample, a light source below the vessel to emit first illumination light toward an inside of the vessel, and a light-receiving member that receives scattered light being the first illumination light scattered by the medium. The light-receiving member includes a light-transmissive portion and a light-receiving portion and is located between the medium and the light source and overlapping the light source.

17 Claims, 12 Drawing Sheets

(51) Int. Cl.
  *G01N 21/51* (2006.01)
  *G02B 21/06* (2006.01)

(58) Field of Classification Search
  CPC ..... G01N 2021/015; G01N 2021/0314; G01N 2021/4709; G01N 2021/473; G01N 2021/513; G01N 21/03; G01N 21/47; G01N 21/51
  See application file for complete search history.

(56) References Cited

U.S. PATENT DOCUMENTS

| | | | |
|---|---|---|---|
| 2016/0209328 A1* | 7/2016 | Berndt | G01N 15/06 |
| 2017/0357843 A1* | 12/2017 | Chen | G06V 40/1365 |
| 2018/0284019 A1* | 10/2018 | Ude | C12M 27/16 |
| 2019/0011351 A1* | 1/2019 | Izutani | G01B 11/08 |
| 2019/0218500 A1* | 7/2019 | Takimoto | G16B 50/30 |
| 2019/0366329 A1* | 12/2019 | John | G01N 21/01 |
| 2020/0318058 A1 | 10/2020 | Mochizuki et al. | |
| 2022/0349869 A1* | 11/2022 | Clements | G01N 33/48735 |
| 2022/0356435 A1* | 11/2022 | Watanabe | G01N 15/06 |

FOREIGN PATENT DOCUMENTS

| | | |
|---|---|---|
| JP | 2011-257691 A | 12/2011 |
| JP | 2019-106944 A | 7/2019 |
| JP | 6543002 B2 | 7/2019 |

OTHER PUBLICATIONS

Schneider, K., Schütz, V., John, G.T. et al. Optical device for parallel online measurement of dissolved oxygen and pH in shake flask cultures. Bioprocess Biosyst Eng 33, 541-547 (2010). https://doi.org/10.1007/s00449-009-0367-0 (Year: 2010).*

Wittmann, C., Kim, H.M., John, G et al. Characterization and application of an optical sensor for quantification of dissolved O2 in shake-flasks. Biotechnology Letters 25, 377-380 (2003). https://doi.org/10.1023/A:1022402212537 (Year: 2003).*

* cited by examiner

SAMPLE OBSERVATION APPARATUS

TECHNICAL FIELD

The present disclosure relates to a sample observation apparatus for observation of a sample such as a cell in a medium such as a cell culture medium.

BACKGROUND OF INVENTION

In observing samples using a large sample observation apparatus including lenses such as a microscope, many samples located in a limited space such as inside an incubator are difficult to observe at a time. With a known technique for downsizing a sample observation apparatus, for example, light emitted from a light source located lateral to a sensor is reflected and is received by the sensing surface of a sensor to generate an image (refer to, for example, Patent Literature 1).

CITATION LIST

Patent Literature

Patent Literature 1: Japanese Patent No. 6543002

SUMMARY

In an aspect of the present disclosure, a sample observation apparatus includes a transparent vessel that accommodates a medium containing a sample, a light source below the vessel to emit illumination light toward an inside of the vessel, and a light-receiving member that receives scattered light being the illumination light scattered by the medium. The light-receiving member includes a light-transmissive portion and a light-receiving portion and is located between the medium and the light source and overlapping the light source.

In another aspect of the present disclosure, a sample observation system includes a plurality of the above sample observation apparatuses, a plurality of control devices each connected to a corresponding sample observation apparatus of the plurality of sample observation apparatuses to control a sample observation operation of the corresponding sample observation apparatus, and a monitoring device that communicates with the plurality of control devices and outputs monitoring information about the plurality of sample observation apparatuses.

BRIEF DESCRIPTION OF THE DRAWINGS

The objects, features, and advantages of the present invention will become more apparent from the following detailed description and the drawings.

DESCRIPTION OF EMBODIMENTS

A sample observation apparatus according to one or more embodiments of the present disclosure will now be described with reference to the drawings.

Sample Observation Apparatus

First Embodiment

Figure 1A:
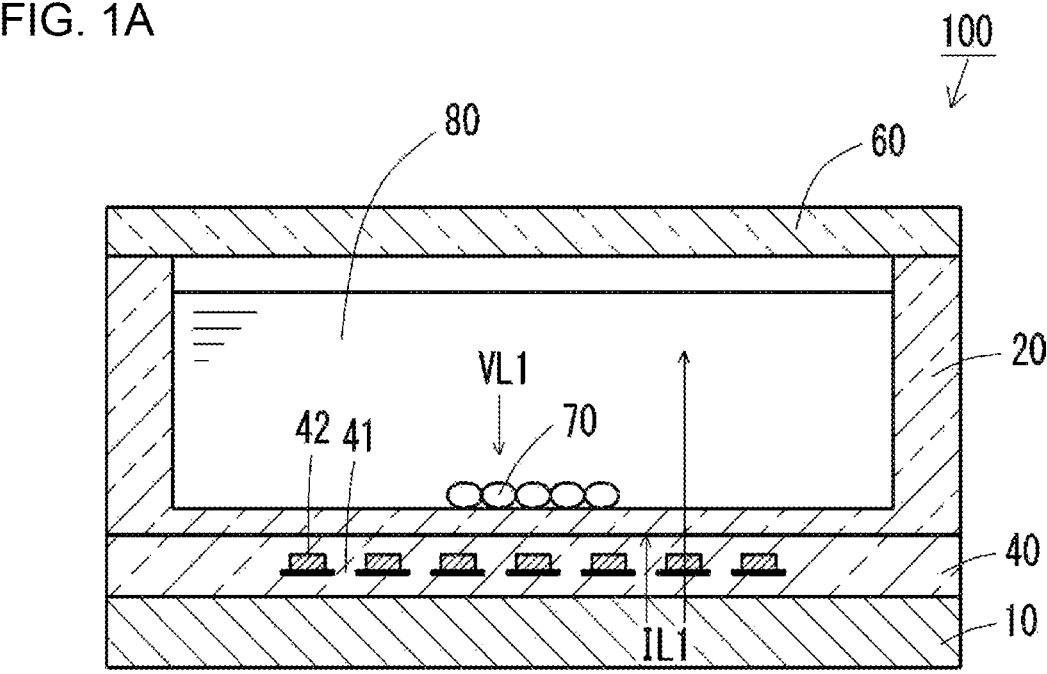
FIG. 1A is a schematic cross-sectional view of a sample observation apparatus according to an embodiment of the present disclosure.
Figure 1B:
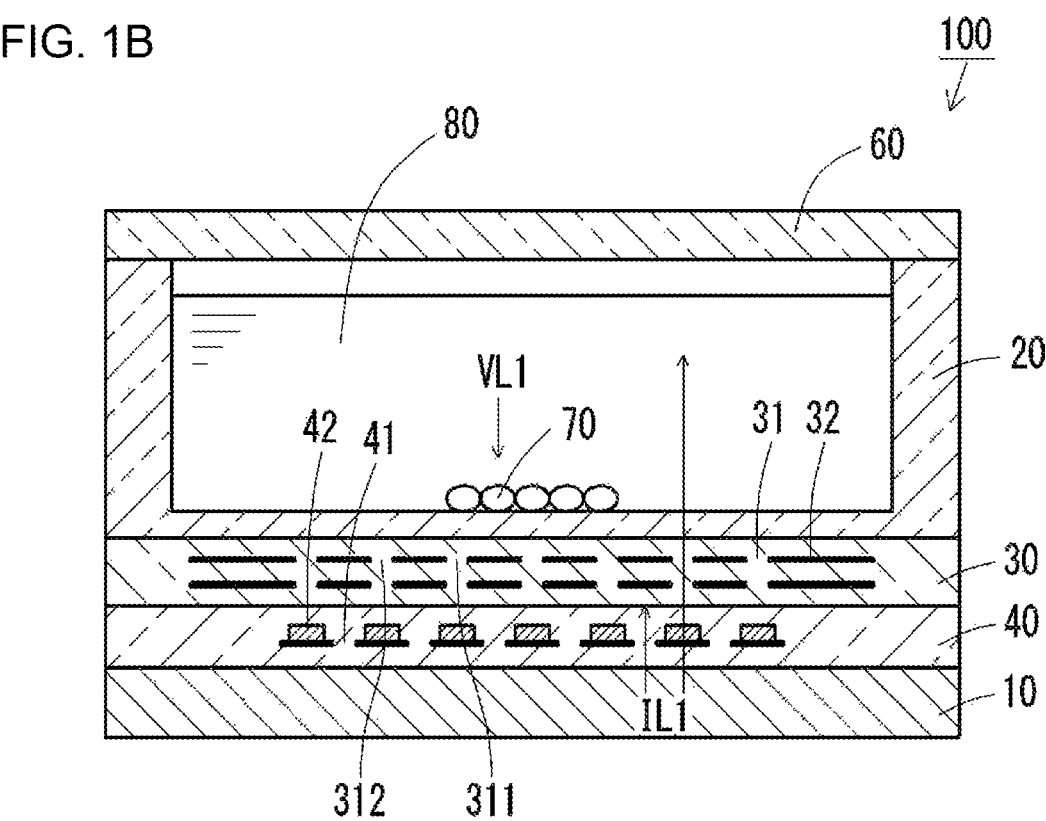
FIG. 1B is a schematic cross-sectional view of a sample observation apparatus according to the embodiment of the present disclosure.

FIGS. 1A and 1B are schematic cross-sectional views of a sample observation apparatus 100 according to a first embodiment. In the first embodiment, the sample observation apparatus 100 includes a light source 10, a vessel 20, and a light-receiving member 40. FIG. 1B illustrates a variation of the structure illustrated in FIG. 1A. As illustrated in FIG. 1B, the sample observation apparatus 100 may include a slit member 30 located between a medium 80 and the light-receiving member 40. In the structure including the slit member 30, slits 31 may be at positions corresponding to light-receiving portions 42 in the light-receiving member 40. This reduces, for example, the likelihood of a light-receiving portion 42 receiving light scattered by, for example, a cell wall to be received by an adjacent light-receiving portion 42. The slit member 30 includes the slits 31 and light shields 32. The light-receiving member 40 includes light-transmissive portions 41 and the light-receiving portions 42.

In the structure illustrated in FIG. 1A, the light-receiving member 40 may be in close contact with the vessel 20 and with the light source 10. This allows the sample observation apparatus 100 to be thinner and smaller. The structure with no space between components also reduces attenuation of light emitted from the light source 10. In the structure illustrated in FIG. 1B as well, the vessel 20, the slit member 30, the light-receiving member 40, and the light source 10 may be in close contact with one another.

In the sample observation apparatus 100, the light-receiving member 40 is located between the medium 80 and the light source 10. This allows the light-receiving member 40 to be placed in an extremely narrow portion or space between the medium 80 and the light source 10. The sample observation apparatus 100 and a sample observation system 101 can thus be compact. Additionally, the light source 10 that emits illumination light into the vessel 20 is located below the vessel 20. This allows samples 70 and the medium 80 to be uniformly illuminated with light to produce an image with uniform quality.

The light source 10 emits first illumination light IL1 toward the medium 80 in the vessel 20. The light source 10 may be, for example, a light-emitting device such as a light-emitting diode (LED), an electroluminescent device (EL device), a fluorescent lamp, or a laser light emitter such as a semiconductor laser element. The light source 10 may be a surface emitting light source including a matrix array of, for example, multiple LEDs, organic EL elements, inorganic EL elements, or semiconductor laser elements. The light source 10 may also include a diffuser plate or a light guide plate. The light source 10 including a light guide plate may emit light from at least one light emitter located on an end face of the light guide plate.

In the variation, the light source 10 faces the slit member 30 with the light-receiving member 40 in between. This allows the light source 10, the slit member 30, and the light-receiving member 40 to be placed in a small space instead of occupying a larger space.

Figure 2:
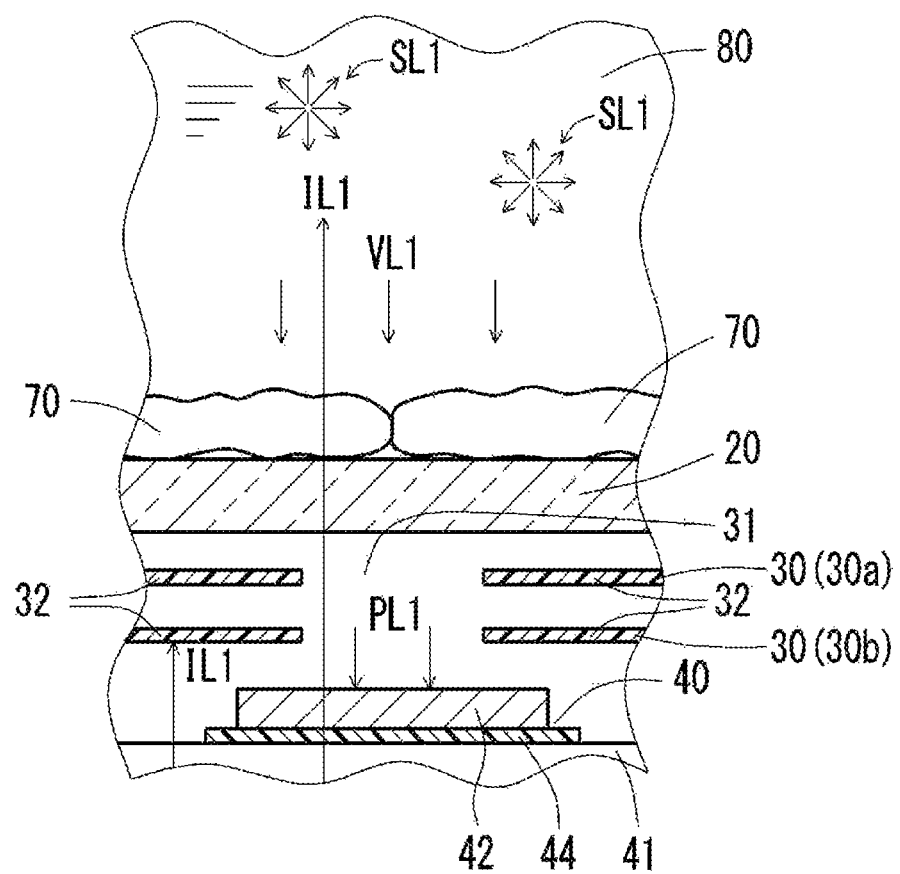
FIG. 2 is a partially enlarged cross-sectional view of a sample observation apparatus according to the embodiment of the present disclosure.
Figure 3:
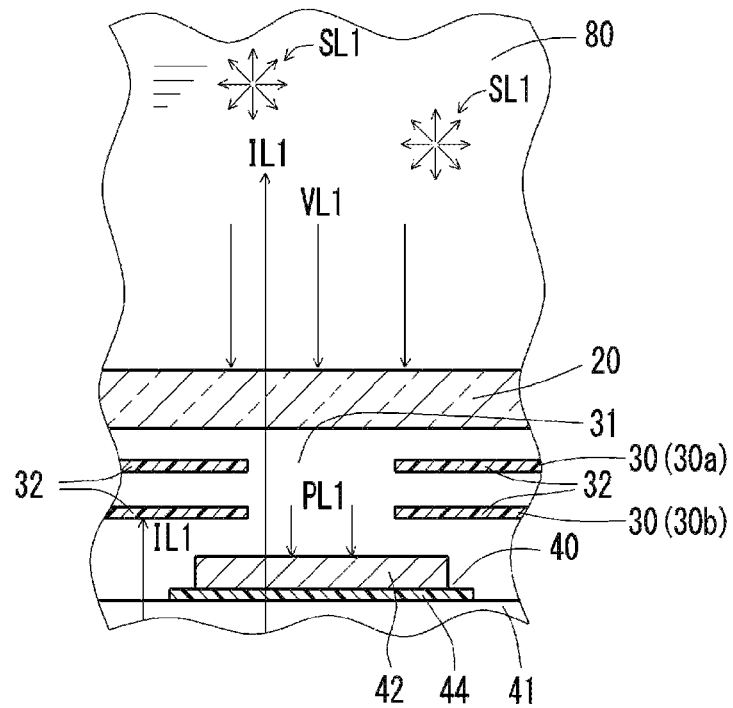
FIG. 3 is a partially enlarged cross-sectional view of the sample observation apparatus according to the embodiment of the present disclosure.

As illustrated in FIGS. 2 and 3, the illumination light IL1 emitted from the light source 10 (hereafter also referred to as first illumination light) is partially transmitted through the light-transmissive portions 41 in the light-receiving member 40, and is scattered in the medium 80 held in the vessel 20. First scattered light SL1 contains first vertical light VL1 vertical to the horizontal surface. The first vertical light VL1 is partially received by the light-receiving portions 42 in the light-receiving member 40 after traveling through the slits 31 in the slit member 30. The first vertical light VL1 is scattered upon hitting the samples 70. In the structure with the slits 31, less first traveling light PL1 travels through the slits 31 when a sample 70 is located above a slit 31 (FIG. 2) than when no sample 70 is located above the slit 31 (FIG. 3). Thus, the intensity of the first vertical light VL1 scattered by the sample 70 can be detected as a difference in the intensity of detected light. This allows detection of any sample 70 located above the slit 31. Formula 1 represents the amount of light I1 received by the light-receiving portion 42 when no sample 70 is located above the slit 31. Formula 2 represents the amount of light IV received by the light-receiving portion 42 when a sample 70 is located above the slit 31.

$$I_0 - B = I_1 \quad (1)$$

$$I_0 - (B+A) - SL = I_1' \quad (2)$$

In these formulas, $I_0$ is the amount of the first vertical light VL1, A is the amount of light absorbed by the sample 70, B is the amount of light absorbed by the medium 80, SL is the amount of light scattered by the sample 70, and $I_1$ and $I_1'$ are the amount of light received by the light-receiving portion 42. The term $I_0-(B+A)$ indicates the amount of light transmitted through the sample 70 and traveling straight without being scattered.

The light source 10 is located below the vessel 20. Thus, the distance between the sample 70 and the light source 10 and the distance between the sample 70 and the light-receiving member 40 are both shorter than when the light source 10 is located above or lateral to the vessel 20, allowing the sample 70 to be detected with high sensitivity. As illustrated in FIG. 2, the first vertical light VL1 is transmitted through the light-receiving member 40 and is then incident on the boundary surface between the sample 70 and the medium 80 (a cell wall surface in a cell) substantially perpendicularly. The above boundary surface regularly reflects the first vertical light VL1 to produce a reflection component at high reflectance, allowing the light-receiving member 40 to receive the first vertical light VL1 with high light intensity. This allows the sample 70 to be detected with high sensitivity.

The light-receiving portions 42 in the light-receiving member 40 include, for example, an amorphous silicon layer as a photoelectric conversion layer with a thickness of not less than about 600 nm, and thus are not light-transmissive at least in the visible light region. However, a thinner photoelectric conversion layer may transmit light in the visible light region. In such a case, the light-transmissive portions 41 may be defined as portions with higher light transmittance than the light-receiving portions 42 with a transmittance of about 80 to 90%.

As illustrated in FIGS. 2 and 3, the light-receiving member 40 may include a light-shielding member 44 facing the light source 10. This reduces the likelihood of the first illumination light IL1 from the light source 10 being received by the light-receiving member 40, thus either complicating or disabling detection of the first vertical light VL1. When the light-receiving member 40 is a plate, the light-shielding member 44 may be stacked as a layer on the surface facing the light source 10 of the light-receiving member 40. The light-shielding member 44 may be, for example, a black resin layer (black matrix) containing black pigment or dye, a black metal layer such as a chromium (Cr) layer, or a colored glass plate or colored plastic plate in black or other dark color. The light-shielding member 44 may also be, for example, a black metal film or a black metal sheet. The light-shielding member 44 may also be, for example, a slightly reflective metal film or a metal sheet for preventing the first illumination light IL1 from entering the light-receiving portions 42.

The light-shielding member 44 may include the light-receiving portions 42 as viewed in plan. In other words, in a plan view, the outline of the light-shielding member 44 may be larger than the outline of the light-receiving portion 42. This more effectively reduces the likelihood of the first illumination light IL1 from the light source 10 being received by the light-receiving member 40, preventing complicating or disabling detection of the first vertical light VL1.

Each light-receiving portion 42 may include a lower electrode, a photoelectric conversion layer located on the lower electrode, and an upper electrode located on the photoelectric conversion layer, with the lower electrode also serving as a light-shielding member 44. This structure includes no light-shielding member 44 other than the light-receiving member 40, allowing the light-receiving member 40 to be thinner. For example, the lower electrode is made of molybdenum or aluminum, the photoelectric conversion layer is made of an amorphous silicon layer, and the upper electrode is made of indium tin oxide (ITO).

The slits 31 and the light-receiving portions 42 may overlap each other as viewed in plan. Thus, the light-receiving portions 42 can receive the first traveling light PL1 traveling through the slits 31 with high sensitivity. In addition, the difference (Ip0–Ip1) between the intensity of light received by the light-receiving portions 42 when the samples 70 are located above the slits 31 (a current value resulting from photoelectric conversion, expressed as Ip1) and the intensity of light received by the light-receiving portions 42 when no samples 70 are located above the slits 31 (a current value resulting from photoelectric conversion, expressed as Ip0) can be greater.

Figure 1C:
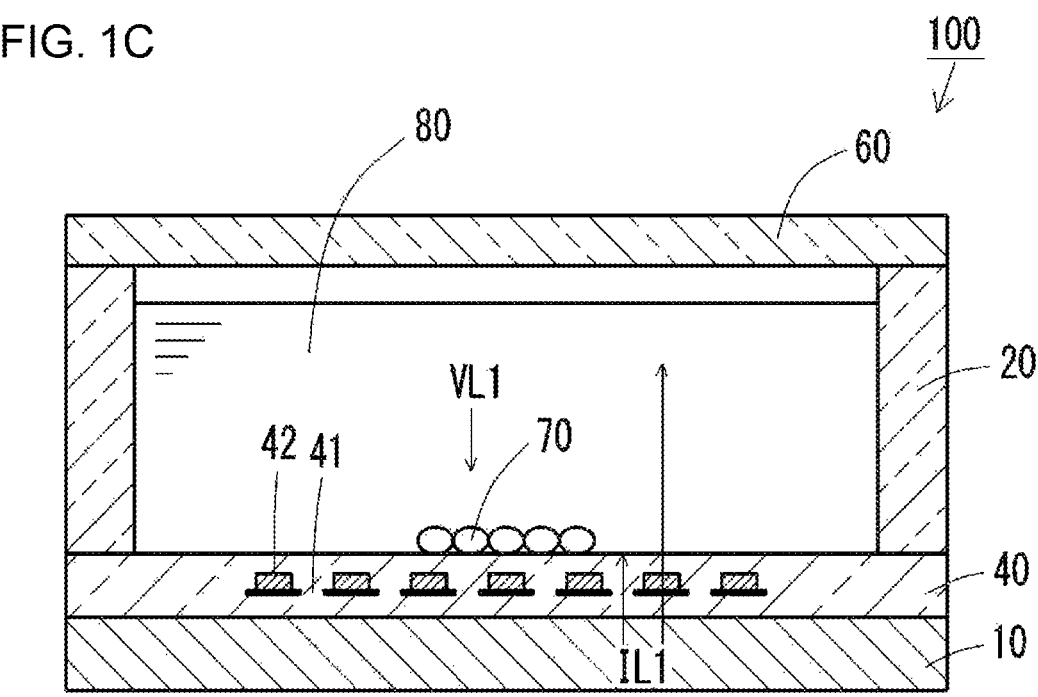
FIG. 1C is a schematic cross-sectional view of a sample observation apparatus according to the embodiment of the present disclosure.

The vessel 20 accommodates the samples 70 and the medium 80. The vessel 20 is made of an optically transparent material, such as a plastic material or a glass material to be observable from outside. The vessel 20 may have any shape and size. The vessel 20 may include a lid 60 and multiple vessel sections for accommodating the samples 70 and the medium 80. The vessel 20 may include a bottom or no bottom as illustrated in FIG. 1C. The vessel 20 with no bottom may be in close contact with the light-receiving member 40 to hold the medium 80. When the vessel 20 includes no bottom, the attenuation of the first illumination light IL1 emitted from the light source 10 is smaller, and the light-receiving member 40 can receive the first vertical light VL1 more efficiently. The vessel 20 with no bottom including the slit member 30 may be in close contact with the slit member 30 to hold the medium 80. The vessel 20 may include a bottom detachable from the vessel body. Thus, for example, the slit member 30 may be attached to the upper surface (surface closer to the medium 80) or the lower surface (surface farther from the medium 80) of the bottom detached from the vessel body. The bottom with the slit member 30 can be attached to the vessel body before use. The light-receiving member 40 can also be attached to the bottom in the same or similar manner. In other words, the slit member 30 and the light-receiving member 40 can be attached to the bottom more easily.

The vessel 20 without accommodating the samples 70 and the medium 80 may be attached to the sample observation apparatus 100 and then receive the samples 70 and the medium 80. The vessel 20 accommodating the samples 70 and the medium 80 may be attached to the sample observation apparatus 100. The vessel 20 can be removed from the sample observation apparatus 100 once the observation is complete. After the samples 70 and the medium 80 are collected, the vessel 20 may be washed and reattached to the sample observation apparatus 100 for another use. In other words, the vessel 20 may be detachable from the sample observation apparatus 100. The vessel 20 may also be detachable from the light source 10. More specifically, the sample observation apparatus 100 may include an attachment 21 (illustrated in FIG. 10) that allows the vessel 20 to be detached from and attached to the light source 10. The attachment 21 may be a box-like or tray-like holder that receives the light source 10, and may include, for example, sidewalls or steps on the periphery of its bottom surface to receive the bottom of the vessel 20.

The slit member 30 may allow the first vertical light VL1 alone that is vertical to the horizontal surface to travel through in the first scattered light SL1, which is the first illumination light IL1 emitted from the light source 10 and then scattered by the medium 80 in the vessel 20. The first traveling light PL1 is the component of the first vertical light VL1 traveling through the slits 31 without being blocked by the light shields 32. The first traveling light PL1 is received by the light-receiving portions 42.

The slit member 30 may include one slit 31 alone or may include multiple slits 31. For the slit member 30 including one slit 31, the slit 31 may be, for example, cross-shaped, spiral-shaped, lattice-shaped, circular, elliptical, triangular, square, or rectangular in a plan view. For the slit member 30 including multiple slits 31, the slits 31 may be, for example, rectangular in a plan view. The slit 31 may have any shape as appropriate for the properties of the sample 70 and the medium 80. The structure with the slit member 30 including multiple slits 31 allows more precise measurement by averaging the measurement values from the multiple slits 31, thus allowing more accurate observation of the samples 70 included in the entire medium 80.

The light shields 32 in the slit member 30 reduce the likelihood of light not vertical to the horizontal surface, of light scattered by the samples 70 and light scattered by the medium 80, traveling through the slits 31 and being received by the light-receiving portions 42. The light shields 32 may be made of, for example, a light-shielding material including a black metal layer such as a chromium (Cr) layer or a black resin layer (black matrix) located in a portion of the lower surface excluding the slits 31. Examples of the transparent substrate include a glass substrate and a plastic substrate. The light shields 32 may be made of a light-shielding material located in a portion of the upper surface of the slit member 30 excluding the slits 31. The light shields 32 may be formed on the surface closer to the light-receiving member 40, on the surface farther from the light-receiving member 40, or on both of the surfaces of the transparent substrate.

As illustrated in FIGS. 2 and 3, the structure may include multiple slit members 30. For example, the structure may include a first slit member 30a located closer to the vessel 20 and a second slit member 30b located closer to the light source 10. The second slit member 30b may have its upper surface at a distance from the bottom surface of the first slit member 30a to more effectively block light scattered by the samples 70. The first slit member 30a and the second slit member 30b may have substantially the same shape and may be located at substantially the same position in a plan view. The second slit member 30b may have its upper surface at a distance of 1 to 100 µm from the bottom surface of the first slit member 30a. This structure sufficiently blocks light scattered by the samples 70. This effectively reduces the likelihood of the light scattered by the samples 70 traveling through the first slit member 30a and the second slit member 30b and being received by the light-receiving portions 42. This also reduces the likelihood of the light scattered by, for example, the cell walls of cells located immediately above a slit 31 (e.g., a slit 311) being received by the light-receiving member 40 immediately below another slit 31 adjacent to the slit 311 (e.g., a slit 312). In other words, this structure may reduce the likelihood of signal interference or crosstalk between the adjacent slits 311 and 312.

The light-receiving member 40 is located between the light source 10 and the slit member 30. The light-receiving member 40 partially transmits the first illumination light IL1 emitted from the light source 10, and receives the first traveling light PL1 that has traveled through the slit member 30. The light-receiving member 40 may have dimensions in the width and length directions larger than those of the slit member 30. The light-receiving member 40 and the slit member 30 may also be formed as an integral substrate.

Figure 4:
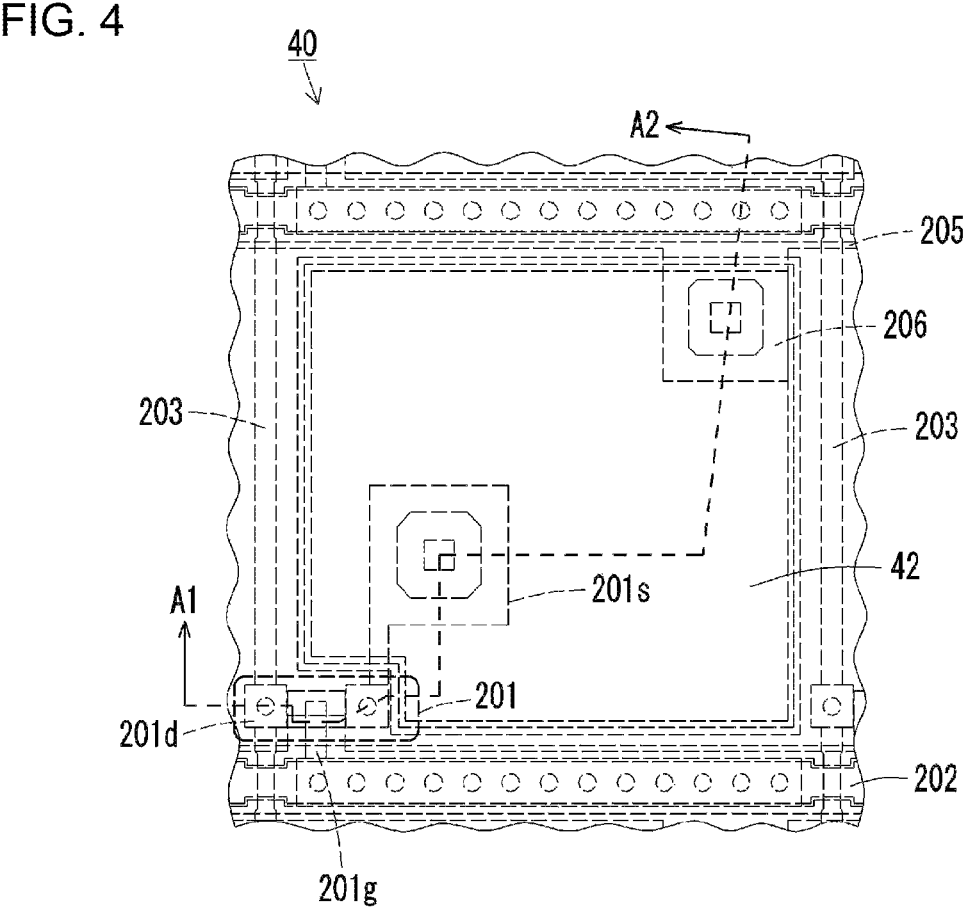
FIG. 4 is a plan view of a light receiver in a sample observation apparatus according to the embodiment of the present disclosure.
Figure 5:
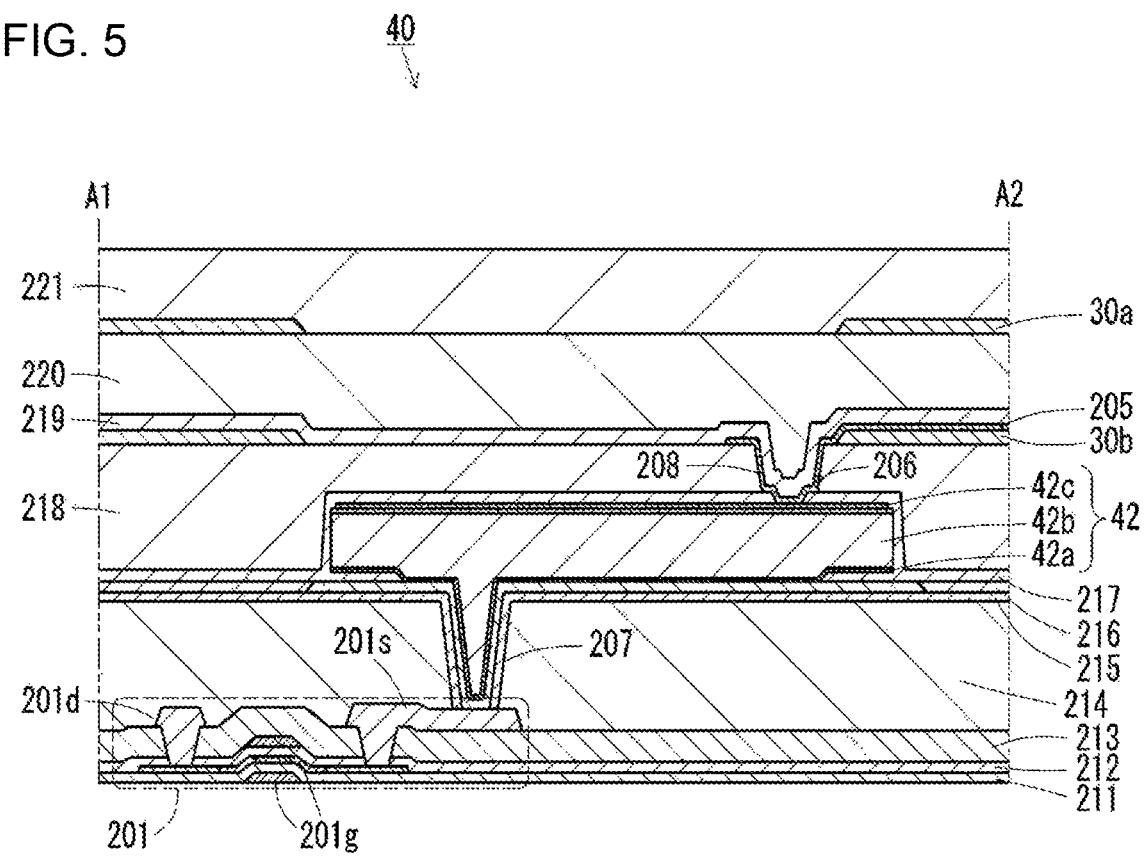
FIG. 5 is a cross-sectional view of the light receiver in the sample observation apparatus according to the embodiment of the present disclosure.

The light-receiving member 40 includes the light-transmissive portions 41 that transmit the first illumination light IL1 emitted from the light source 10, and the light-receiving portions 42 that receive the first traveling light PL1. The light-transmissive portions 41 may be, for example, made of a transparent substrate, such as a glass substrate or a plastic substrate. The light-receiving portions 42 may include, for example, a light receiving element such as a silicon photodiode. Photodiodes can be mass-produced at lower costs using thin-film technologies including thin-film transistors. The light-receiving portions 42 may be located on the upper surface of a base made of a glass substrate or a plastic substrate. FIGS. 4 and 5 illustrate an example light-receiving member 40.

As illustrated in FIG. 4, the light-receiving member 40 includes a light-receiving portion 42 that is, for example, a PIN photodiode, a thin film transistor (TFT) 201 that switches to extract, as a signal, an electric charge obtained through photoelectric conversion performed by the light-receiving portion 42, and a bias electrode 206 that supplies a constant bias voltage to the light-receiving portion 42. The TFT 201 includes gate electrodes 201g, a source electrode 201s, and a drain electrode 201d. The gate electrodes 201g are connected to a gate wire 202, and the drain electrode 201d is connected to a drain wire 203. The bias electrode 206 is connected to a bias wire 205.

As illustrated in FIG. 5, the light-receiving member 40 includes first to eleventh insulating layers 211 to 221 sequentially stacked on one another on a substrate such as a glass substrate. The first to eleventh insulating layers 211 to 221 are inorganic insulating layers including, for example, silicon oxide ($SiO_2$) or silicon nitride ($Si_3N_4$), or organic insulating layers including, for example, an acrylic resin or a polycarbonate resin. For example, the first to third insulating layers 211 to 213, the fifth to seventh insulating layers 215 to 217, and the ninth insulating layer 219 are thin insulating layers that may be inorganic insulating layers. The fourth insulating layer 214, the eighth insulating layer 218, the tenth insulating layer 220, and the eleventh insulating layer 221 are thick insulating layers that may be organic insulating layers.

The TFT 201 is located between the first insulating layer 211 and the second insulating layer 212, and between the second insulating layer 212 and the third insulating layer 213, directly formed with a film deposition method such as chemical vapor deposition (CVD). The source electrode 201s is connected to a lower electrode 42a in the light-receiving portion 42 through a through-hole 207. The TFT 201 is a double gate TFT that includes the gate electrodes 201g at the top and the bottom of the gate portion of to semiconductor layer but may also be a single gate TFT. The light-receiving portion 42 is formed with a thin-film formation method between the sixth insulating layer 216 and the seventh insulating layer 217. The light-receiving portion 42 includes the lower electrode 42a made of, for example, aluminum, a semiconductor layer 42b as a photoelectric conversion layer made of, for example, amorphous silicon on the lower electrode 42a, and an upper electrode 42c that is a transparent electrode such as an ITO electrode on the semiconductor layer 42b. The upper electrode 42c is connected to the bias wire 205 with the bias electrode 206 and a through-hole 208.

Although the first slit member 30a and the second slit member 30b are directly formed with the thin-film formation method as layers stacked above the light-receiving portion 42 in the example structure in FIG. 5, the light-receiving portion may have any other structure.

The light-receiving member 40 may be located on the bottom surface of the vessel 20. In this case, the slit member 30 may be located immediately above the light-receiving member 40. In this case, the slit member 30 and the light-receiving member 40 are located in the medium 80 accommodated in the vessel 20. The slit member 30 and the light-receiving member 40 may be disposable products to eliminate the burden of washing and removing the samples 70 and the medium 80.

The light-receiving member 40 may be located between the light source 10 and the vessel 20. In this structure, the slit member 30 may be located on the bottom surface of the vessel 20. In this structure, the slit member 30 is located in the medium 80 accommodated in the vessel 20. This structure avoids adherence of the samples 70 and the medium 80 to the light-receiving member 40. The light-receiving member 40 is thus reusable without being washed. The slit member 30 may be a disposable product to eliminate the burden of washing and removing the samples 70 and the medium 80.

The light-receiving member 40 may have the upper surface at a distance of 50 to 1000 μm from the bottom surface of the slit member 30. This structure allows light scattered by the samples 70 and traveling through the slits 31 in the slit member 30 to travel without reaching the light-receiving portions 42. This reliably prevents the light-receiving portions 42 from receiving the scattered light. This structure can thus detect the samples 70 more accurately.

Figure 6:
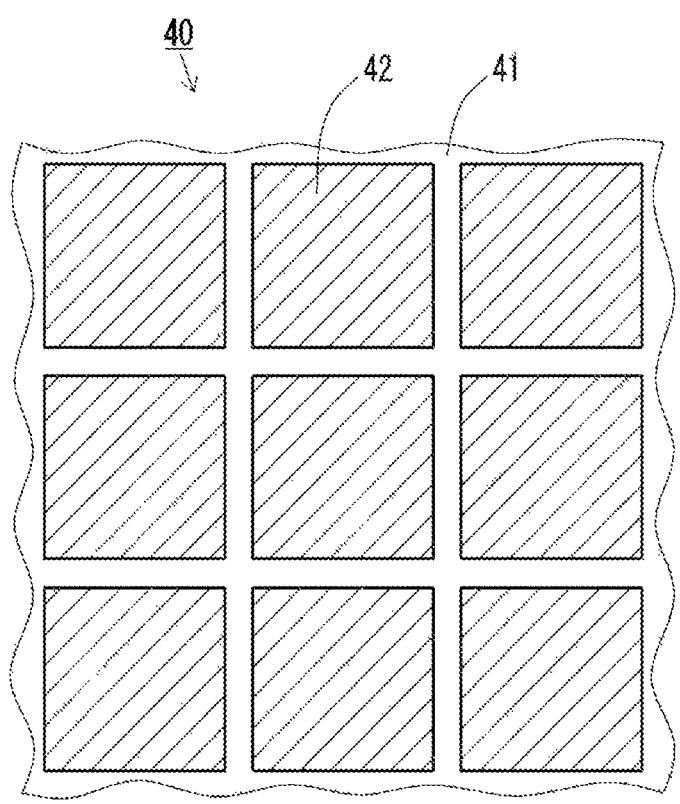
FIG. 6 is a plan view of an example light receiver in the sample observation apparatus according to the embodiment of the present disclosure.
Figure 7:
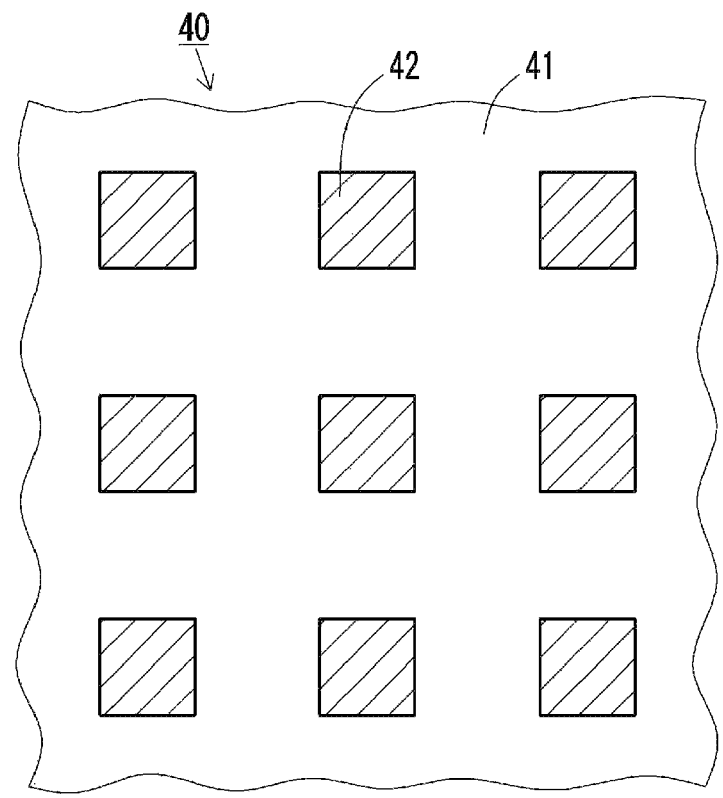
FIG. 7 is a plan view of an example light receiver in the sample observation apparatus according to the embodiment of the present disclosure.

The light-receiving member 40 may include a single light-transmissive portion 41 and multiple light-receiving portions 42. As illustrated in FIGS. 6 and 7, the multiple light-receiving portions 42 may have a square shape in a plan view, and the light-transmissive portion 41 may have an area larger than the total area of the light-receiving portions 42 (FIG. 7). Setting the area of the light-transmissive portion 41 larger than the total area of the light-receiving portions 42 allows the first illumination light IL1 to be sufficiently transmitted and sufficiently scattered by the medium 80 to sufficiently illuminate the samples 70. The light-receiving portions 42 may be rectangular, circular, oval, hexagonal, in another polygonal shape, or in any other shape as viewed in plan. The light-receiving portions 42 may be in any shape symmetric with respect to a line or a point. This allows the light-receiving portions 42 to receive light with less unevenness in characteristics and distribution as viewed in plan. More specifically, the light-receiving portions 42 may have a hexagonal shape in a plan view suitable for their closest arrangement and thus may be suitable for obtaining high resolution.

The number of light-receiving portions 42 may be the same as the number of slits 31. The light-receiving portions 42 may have dimensions in the width and length directions substantially equal to those of the slits 31. Each light-receiving portion 42 may be located at substantially the same position as the corresponding slit 31 in the width and length directions in a plan view. Multiple light-receiving portions 42 may correspond to a single slit 31. In this case, an address may be assigned to each of the light-receiving portions 42 or each of the signals obtained by the multiple light-receiving portions 42 to allow identification of signals for each slit 31.

Figure 8:
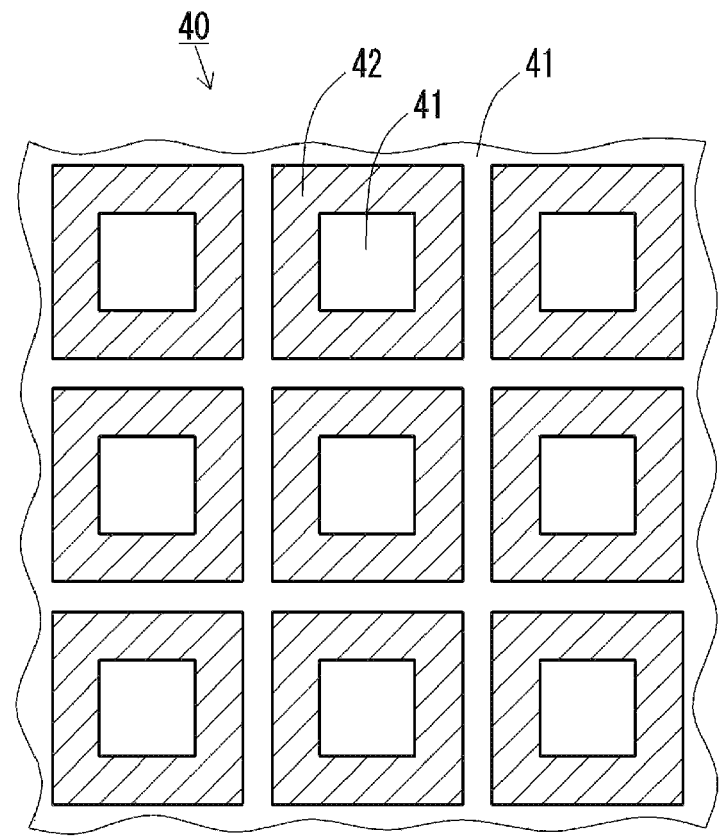
FIG. 8 is a plan view of an example light receiver in the sample observation apparatus according to the embodiment of the present disclosure.

As illustrated in FIG. 8, the light-receiving portions 42 may be rectangular frames in a plan view. This allows both the area of each light-transmissive portion 41 to be sufficiently large and light in a wide range to be received, thus allowing the samples 70 to be detected with high sensitivity over a wide range. The light-receiving portions 42 may be frames that are circular, oval, hexagonal, in another polygonal shape, or in any other shape as viewed in plan. The light-receiving portions 42 may be in any shape symmetric with respect to a line or a point. This allows the light-receiving portions 42 to receive light with less unevenness in characteristics and distribution as viewed in plan. More specifically, the light-receiving portions 42 may have a hexagonal frame shape in a plan view suitable for their closest arrangement and thus may be suitable for obtaining high resolution.

Figure 9:
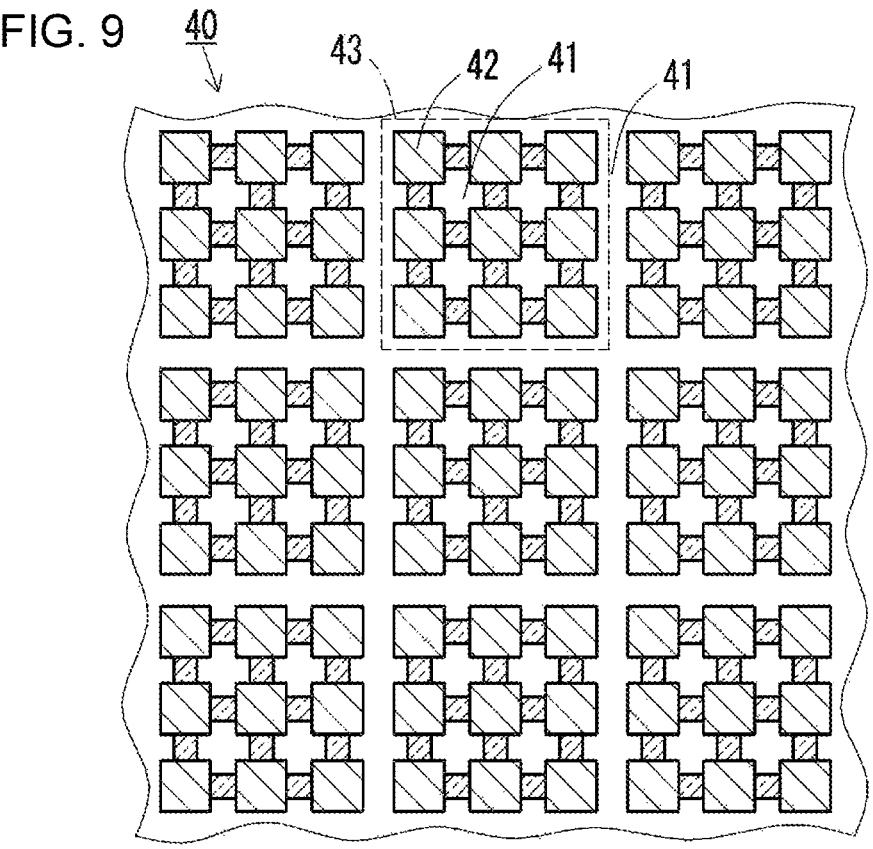
FIG. 9 is a plan view of an example light receiver in the sample observation apparatus according to the embodiment of the present disclosure.

As illustrated in FIG. 9, the light-receiving member 40 may include multiple light-receiving portion units 43 each including a combination of multiple light-transmissive portions 41 and multiple light-receiving portions 42. Each light-receiving portion unit 43 may include light-transmissive portions 41 arranged in a grid in a plan view and multiple light-receiving portions 42 that are square-shaped in plan a view and separated by the grid of light-transmissive portions 41. Each light-receiving portion unit 43 may include four light-transmissive portions 41 arranged in a grid in a plan view and nine light-receiving portions 42 that are square-shaped in a plan view. The square light-receiving portions 42 are connected by anode electrodes. The anode electrodes may be transparent electrodes made of, for example, ITO to achieve higher light transmittance. Thus, with a small total area of the light-receiving portions 42 relative to the total area of the light-transmissive portions 41, light can be received over a wide area in a distributed manner, allowing the samples 70 to be detected with high sensitivity over a wide range. This also increases the total area of the light-transmissive portions 41 in the light-receiving member 40 and allows the medium 80 to be uniformly illuminated by the first illumination light IL'.

In a variation of the present embodiment, a sample observation apparatus 100 may include multiple sets of a light source 10, a slit member 30, and a light-receiving member 40. For example, a first set including a light source 10, a slit member 30, and a light-receiving member 40 may be located below a vessel 20, and a second set including a light source 10, a slit member 30, and a light-receiving member 40 may be located lateral to the vessel 20. The light-receiving member 40 in the second set receives light parallel to the horizontal surface in light scattered by the medium 80. The structure with multiple sets of the light source 10, the slit member 30, and the light-receiving member 40 can detect the samples 70 more accurately.

When the vessel 20 includes multiple vessel sections, each vessel section may include at least one first set. This allows detection of samples 70 in each vessel section. Each vessel section may further include at least one second set. This allows more accurate detection of the samples 70 in each vessel section.

Figure 10:
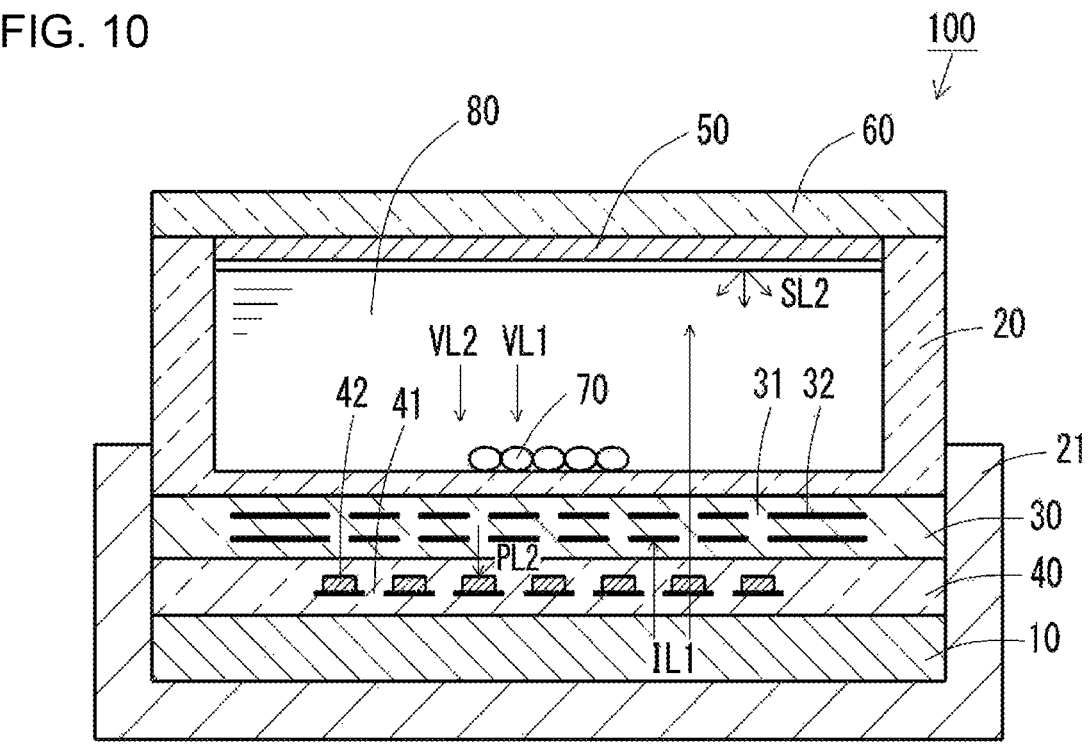
FIG. 10 is a cross-sectional view of a sample observation apparatus according to a variation of the embodiment of the present disclosure.

In a variation of the present embodiment, a sample observation apparatus 100 may include a reflector 50 as illustrated in FIG. 10. The reflector 50 reflects and scatters the first illumination light IL1 toward the medium 80 before the light exits upward from the vessel 20. This improves the utilization efficiency of the first illumination light IL1. The reflector 50 faces the light source 10 with the vessel 20 in between. For example, the reflector 50 may be attached to the inner surface of the lid 60 on the vessel 20. The first illumination light IL1 reflected by the reflector 50 is scattered as second scattered light SL2. Second vertical light VL2 is a component of the second scattered light SL2 vertical to the horizontal surface. Second traveling light PL2 is a component of the second vertical light VL2 traveling through the slit 31 without being blocked by the light shields 32. The second traveling light PL2 is received by the light-receiving portions 42.

The reflector 50 may be made of any material that reflects the first illumination light ILL including, for example, metal foil with high reflectivity, such as aluminum foil or silver foil, and a metal layer with high reflectivity, such as an aluminum layer or a silver layer formed by, for example, vapor deposition. The structure including the reflector 50 allows the second traveling light PL2 in addition to the first traveling light PL1 to be received by the light-receiving portions 42 and thus allows the samples 70 to be detected with high sensitivity.

Figure 14:
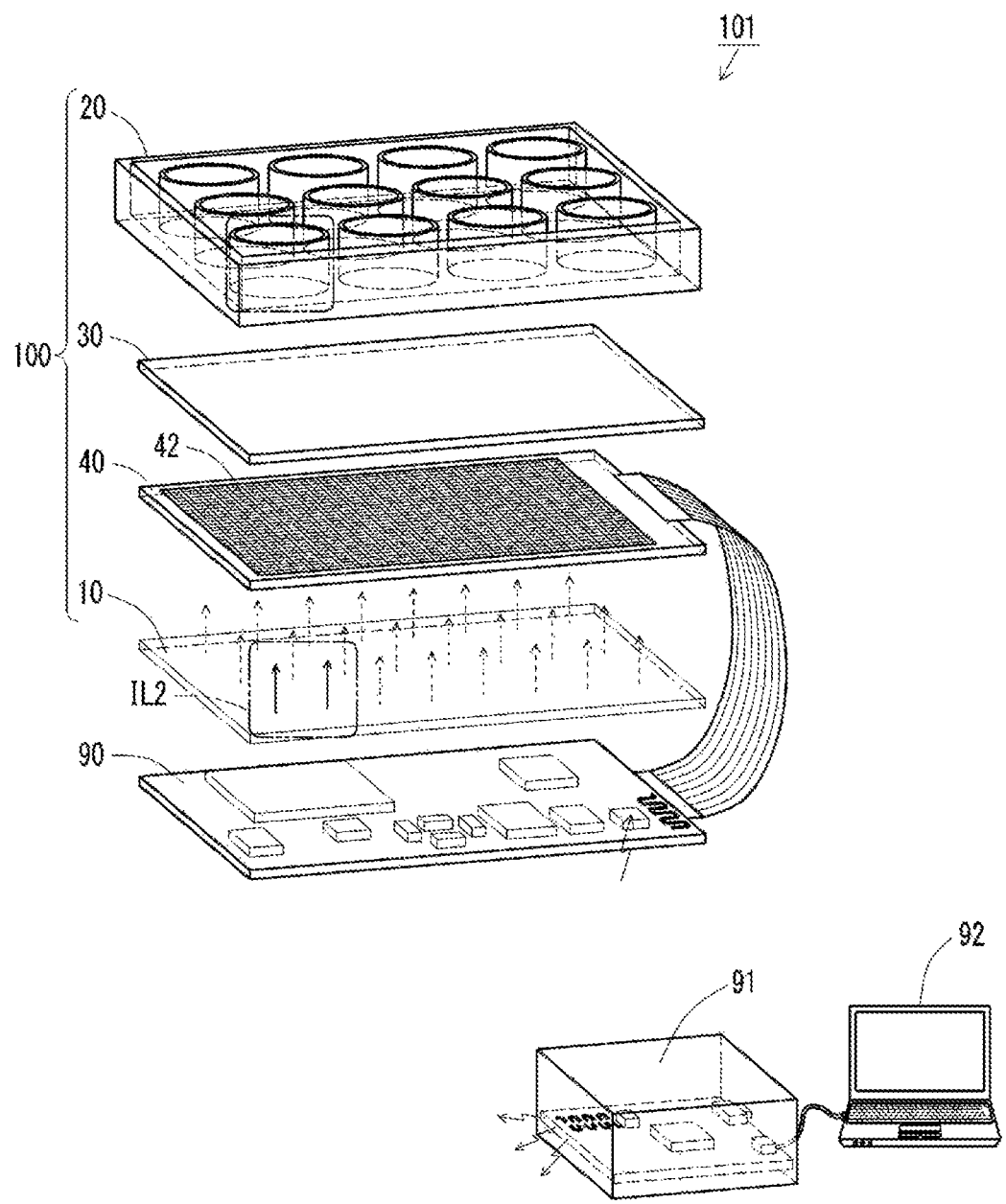
FIG. 14 is an exploded perspective view of a sample observation system according to a variation of the embodiment of the present disclosure.
Figure 15:
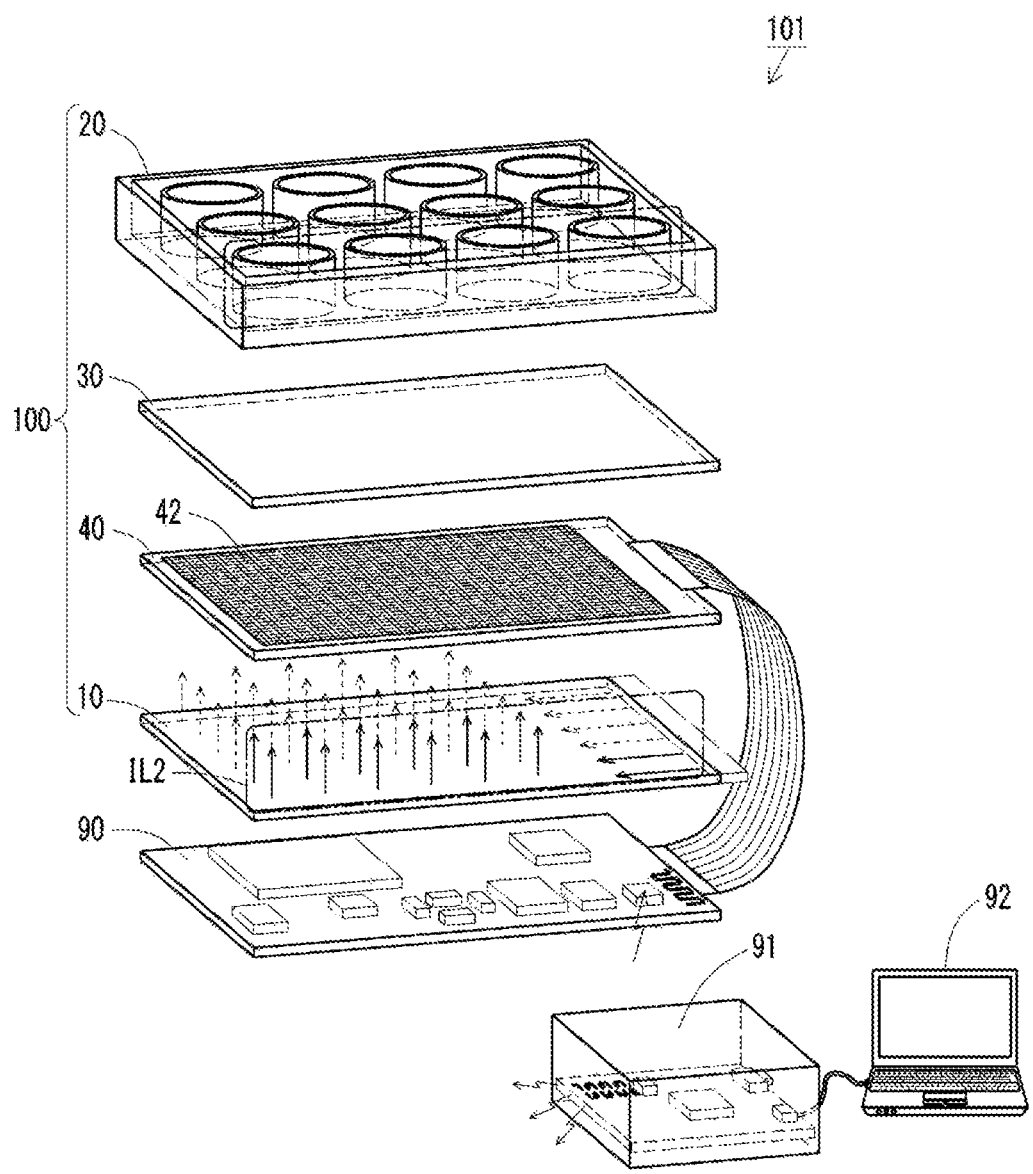
FIG. 15 is an exploded perspective view of a sample observation system according to a variation of the embodiment of the present disclosure.

In a variation of the present embodiment, as illustrated in FIGS. 14 and 15, light from the light source 10 (hereafter also referred to as second illumination light IL2) may illuminate a portion of the vessel 20 alone. When the vessel 20 includes multiple vessel sections, the second illumination light IL2 from the light source 10 may, for example, illuminate vessel sections individually. In other words, the vessel 20 may include multiple vessel sections as multiple target areas for illumination, and the light source 10 may illuminate one or more vessel sections individually. The second illumination light IL2 may illuminate any number of vessel sections at a time. The second illumination light IL2 may illuminate one vessel section after another, or one set of multiple vessel sections after another, or may illuminate individual vessel sections and sets of multiple vessel sections in a predetermined sequence. The entire vessel 20 is not illuminated at a time. The peak power consumption of the light source 10 is thus reduced.

In a variation of the present embodiment, a sample observation apparatus 100 may measure the pH value of a medium 80 with light-receiving portions 42 in a light-receiving member 40. In other words, the light-receiving member 40 may obtain signals based on the transmittance of the light scattered by the medium 80, such as a cell culture medium, in the medium 80 to measure the pH value of the medium 80. In the present variation, the pH value of the medium 80 is varied by the sample 70. The medium 80 contains a pH indicator and the color or transmittance of the medium 80 changes in accordance with changes in the pH value of the medium 80. Light-receiving portions 42 in an area with no samples 70 are unaffected by scattering of light by the samples 70 and are thus suitable for measuring changes in the transmittance of the medium 80. The measured transmittance is compared with a precreated look-up table of transmittance and pH values to calculate the pH value of the medium 80. The pH value can also be measured based on a change in the absorbance or optical density (OD) of the medium 80 instead of a change in the transmittance of the medium 80.

The light-receiving member 40 that obtains signals for measuring the pH value of the medium 80 may obtain signals from a light-receiving portion 42 in an area with no samples 70 in the medium 80, or signals from a sample-free area. A reference signal from a sample-free area may be prestored in a look-up table or another storage, and the light-receiving portions 42 in areas with no samples 70 may be identified by comparing signals from each light-receiving portion with the reference signal in the storage.

The light-receiving portions 42 for obtaining signals for measuring the pH value of the medium 80 may be at positions corresponding to the periphery of the medium 80 at which a relatively small amount of the samples 70 is located in a plan view. In the early stage of measurement, a small number of cells as the samples 70 are contained in the medium 80, with substantially no samples 70 being in an area corresponding to the periphery of the medium 80. Throughout the entire period of measurement, the area corresponding to the periphery of the medium 80 is likely to include light-receiving portions 42 with no samples 70.

The vessel 20 may also include a partitioned space that allows the medium 80 to flow in and out but allows no samples 70 to enter. The light-receiving member 40 for obtaining signals for measuring the pH value of the medium 80 may be at a position corresponding to the partitioned space in a plan view. The partitioned space may be separated by a partition wall with an upper end closely below the level of the medium 80, or a partition wall with fine through-holes with a size that allows the medium 80 to travel through but does not allow the samples 70 to travel through. The partitioned space may be at a position corresponding to the periphery of the medium 80 at which a relatively small amount of the samples 70 is in a plan view.

The lookup table herein refers to data indicating the relationship between the absorbance of the medium 80 and the pH value that is, for example, stored in a storage (memory). The storage may be a memory such as a storage circuit (memory circuit), an integrated circuit (IC), and a large-scale integration (LSI) included in a personal computer (PC), a stand-alone mass storage device, or a portable memory device such as a universal serial bus (USB) memory.

For measuring the pH value of the medium 80, the light-receiving portions 42 may be made of an amorphous silicon photodiode with a PIN structure. The PIN photodiode is a three-layered photodiode with an intrinsic layer (I-layer) between a PN junction. The PIN photodiode includes three semiconductors, or p-type, intrinsic, and n-type (PIN) semiconductors, which are joined together. Whereas a PN photodiode includes a depletion layer with no electrons and no holes around a PN junction, a PIN diode includes a prepared I-layer with no electrons and no holes instead of a depletion layer.

The materials for a photodiode may be silicon, germanium, indium, gallium, arsenic, and lead sulfide. These materials are selected as appropriate for the wavelength of light to be detected. Silicon absorbs light at wavelengths of 190 to 1100 nm. Germanium absorbs light at wavelengths of 400 to 1700 nm. Indium, gallium, and arsenic absorb light at wavelengths of 800 to 2600 nm. Lead sulfide absorbs light at wavelengths of 1000 to less than 3500 nm.

Figure 11:
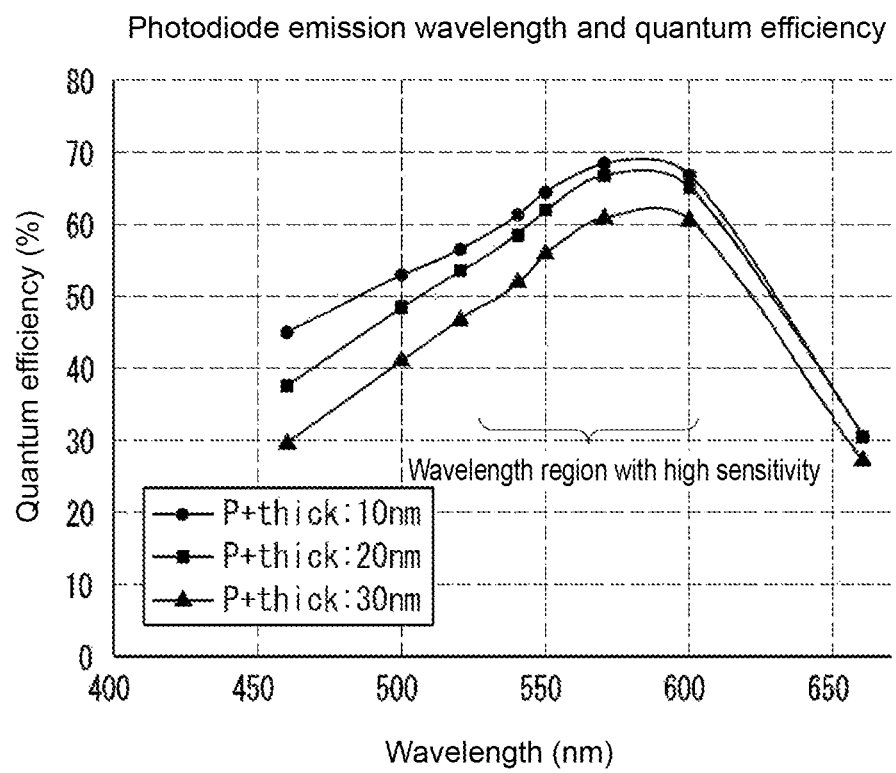
FIG. 11 is a diagram of example quantum efficiency spectra of a light-receiving portion of the light receiver in the sample observation apparatus according to the embodiment of the present disclosure.

Amorphous silicon refers to non-crystalline silicon with a higher absorption coefficient than crystalline silicon. Amorphous silicon photodiodes have the highest quantum efficiency (internal quantum efficiency) at a wavelength of around 560 nm as illustrated in FIG. 11. In FIG. 11, the solid circles represent the quantum efficiency of a P+ layer with a thickness of 10 nm on a light receiving surface, solid squares represent the quantum efficiency of a P+ layer with a thickness of 20 nm, and solid triangles represent the quantum efficiency of a P+ layer with a thickness of 30 nm. As the thickness of the P+ layer increases, the quantum efficiency to light in wavelength regions excluding the wavelength region of green light may tend to decrease. Thus, the thickness of the P+ layer may be 10 nm or greater, or specifically 20 nm or greater, and more specifically 20 to 30 nm.

For measuring the pH value of the medium 80, the absorbance with monochromatic light selectively from the received first traveling light PL1 may be measured. Monochromatic light refers to light with a single wavelength or in a predetermined wavelength region alone and not dividable further in the spectrum. Monochromatic light may be, for example, red light or light in a red wavelength region, blue light or light in a blue wavelength region, and green light or light in a green wavelength region. Monochromatic light may specifically be green light or light in a green wavelength region. The predetermined wavelength region is, for example, a wavelength region centered on a center wavelength. Light in the wavelength region is expressed using the center wavelength plus or minus the bandwidth of the wavelength. Green light may have a wavelength of about 560 nm. A green wavelength region may have a wavelength region of about 560±40 nm, or more specifically, about 560±20 nm. Light in the wavelength region of monochromatic light is received to improve the light sensitivity.

Figure 12:
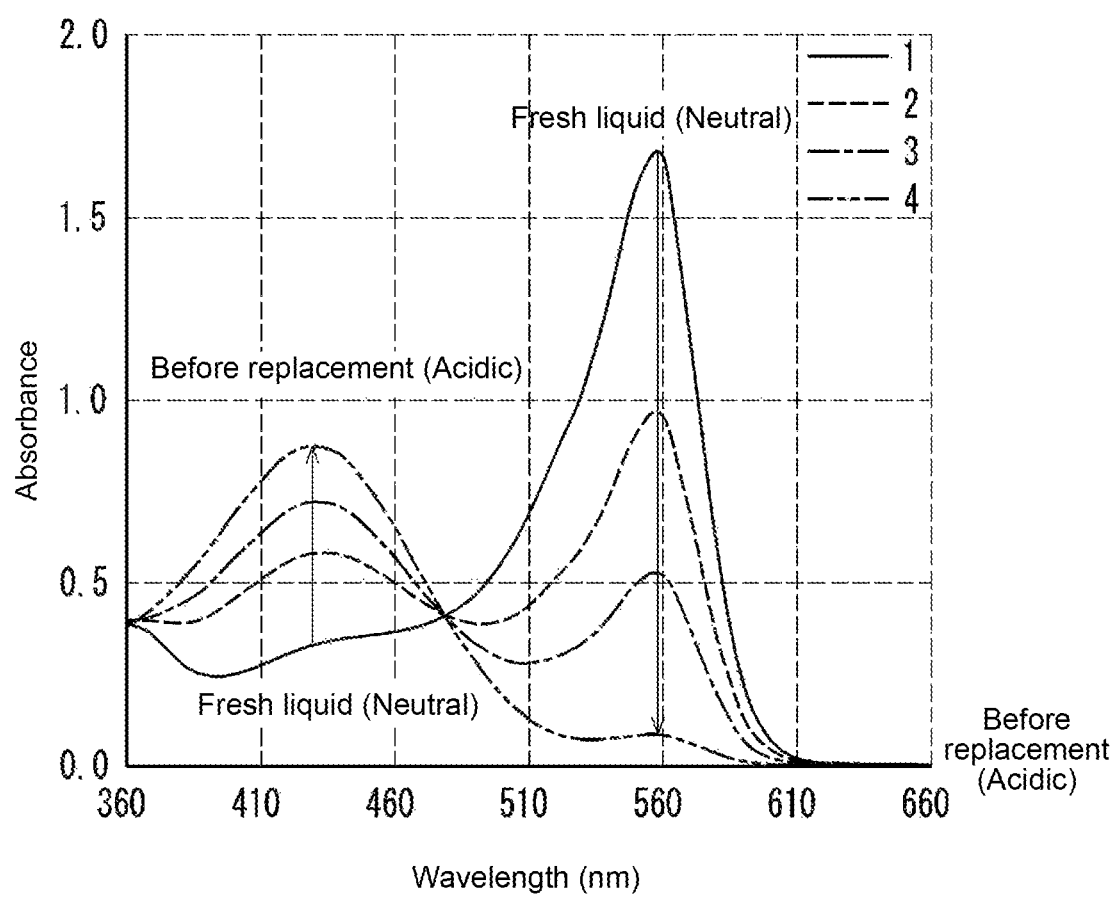
FIG. 12 is a diagram of example absorption spectra of a medium in the sample observation apparatus according to the embodiment of the present disclosure.

FIG. 12 illustrates an example of a change in the absorbance with a change in the pH value of medium 80. In FIG. 12, the absorbance of a fresh medium 80 is indicated by 1 (solid line), the absorbance of the medium 80 with the pH decreasing after a certain time is indicated by 2 (dotted line) and 3 (dot-dash line), and the absorbance of the medium 80 with the pH decreasing further is indicated by 4 (two-dot-dash line).

The pH indicator refers to a reagent that changes color in accordance with a pH value. Examples of the pH indicator include methyl orange, bromophenol blue, bromocresol green, bromothymol blue, phenol red, thymol blue, and phenolphthalein. The pH indicator may be added to the medium 80 in advance to allow measurement of a change in the absorbance in accordance with a change in the pH value of the medium 80, or may be added to the medium 80 immediately before the absorbance of the medium 80 is measured.

The pH indicator may have a lower absorption peak in a predetermined wavelength region as the pH value of the medium 80 decreases, and the light-receiving portions 42 may have the highest quantum efficiency in the above predetermined wavelength region. This allows highly sensitive detection of the decrease in the absorption peak, thus allowing highly sensitive and accurate measurement of the pH value of the medium 80.

The sample observation apparatus 100 according to the present embodiment can detect any sample 70 that is a material to scatter incident light. The sample 70 may be, for example, cells. The cells may be of any type, including animal cells, plant cells, yeast cells, or bacterial cells. Examples of the animal cells include muscle cells, visceral cells such as the liver, blood cells such as lymphocytes, monocytes, and granulocytes, nerve cells, immune cells, and induced pluripotent stem (iPS) cells. These cells may be tissue-derived primary cells or may be subcultured cells. The cells may be prokaryotic cells such as Escherichia coli cells, or eukaryotic cells such as animal cells or plant cells. The cells may be, for example, normal cells, abnormal cells such as tumor cells, or artificially created cells such as transgenic cells. The cells may also be cultured as part of a living tissue. The cell culture may be adherent culture or suspension culture.

The cells may also be stem cells suitable for regenerative medicine. The stem cells may be pluripotent stem cells such as iPS cells, or somatic stem cells such as mesenchymal stem cells (MSCs). iPS cells have pluripotency and the self-renewal ability. iPS cells are produced by introducing several types of genes into somatic cells, such as skin cells of a human, and culturing the cells to be pluripotent cells that can differentiate into cells of various tissues and organs, similarly to embryonic stem (ES) cells. The self-renewal ability allows iPS cells to retain pluripotency after division and proliferation, thus achieving substantially unlimited proliferation. MSCs are human stem cells at various locations throughout the body, including bone marrow, fat, and skin. MSCs can differentiate into fat, bone, and cartilage, and also into tissue cells such as hepatocytes and neurons. MSCs are derived from bone marrow, fat, or others. Unlike iPS cells, MSCs have immunomodulatory effects and lower the likelihood of MSCs being rejected after transplantation. MSCs also have a lower possibility of tumorigenesis. Thus, the cells may be MSCs that may be used in regenerative medicine.

The sample observation apparatus 100 according to the present embodiment can be used to manage the number of proliferated iPS cells and MSCs with high proliferative ability.

The medium 80 may be any liquid or solid material that can hold the samples 70. The medium 80 may be selected as appropriate for the sample 70. For example, when the sample 70 is cells, the medium 80 may be a culture medium. A culture medium (hereafter, also a cell culture medium) provides a growth environment for target cells in cell culture. The culture medium is a source of nutrients such as a carbon source including glucose, a nitrogen source including peptone and ammonium sulfate, and inorganic salts including amino acids, vitamins, and phosphate. The culture medium also provides a scaffold (platform) for cell proliferation. More specifically, the culture medium may be a liquid medium or a solid medium. The liquid medium includes a liquid containing the above nutrients used for cell culture. The solid medium includes the liquid that is then solidified by adding agar or gelatin. In the present embodiment, the sample observation apparatus 100 may use a light-transmissive liquid medium allowing the cells to move in a plane (two-dimensionally) crossing the slits 31. In some embodiments, the sample observation apparatus 100 may include a light-transmissive solid medium allowing the cells to slightly move two-dimensionally or to proliferate three-dimensionally above and overlapping the slits 31.

When cells are used as the sample 70 and a culture medium is used as the medium 80, the vessel 20 may be, for example, a commercially available cell culture vessel such as a Petri dish, a flask, or a multi-well plate. These cell culture vessels typically include lids and are made of a transparent resin. A cell culture vessel has one or more spaces suitable for cell proliferation. For example, a Petri dish may have a width or a diameter of several centimeters to several tens of centimeters and a height of several millimeters to several centimeters. A flask may have a width or a diameter of several centimeters to several tens of centimeters and a height of five to several tens of centimeters. A microwell plate may have a width or a diameter of several centimeters to several tens of centimeters and a height of 0.5 to several centimeters. The microwell plate may have wells each in the shape of, for example, a circle, a rectangle such as a square, or a polygon such as a pentagon or a hexagon in a plan view. The circular well is suitable for isometric proliferation of cells, thus allowing effective proliferation of the cells. The hexagonal well is suitable for the closest arrangement of wells, thus effectively reducing the size of the microwell plate.

In one example described below, the sample observation apparatus 100 according to the present embodiment manages the number of cells.

When cells (sample 70) are proliferated insufficiently in the early stage of cell culture, a small number of cells are contained in the cell culture vessel, and scattering by cells causes a slight decrease of light. The first vertical light VL1 is thus received by the light-receiving portions 42 with substantially no scattering. After sufficient proliferation of the cells, a large number of cells are densely contained in the cell culture vessel. These cells scatter the first vertical light VL1, causing a small amount of light to be received by the light-receiving portions 42. For cells that have undergone sufficient proliferation in the cell culture vessel, the amount of light received by the light-receiving portions 42 corresponding to the number of proliferated cells is measured in advance and stored as a predetermined amount into a storage table in, for example, a memory device. In response to the amount of light received by the light-receiving portions 42 being smaller than or equal to the predetermined amount (greater than or equal to a predetermined number of proliferated cells), the cells are determined to have proliferated to the predetermined number or greater. The predetermined number may be the number of cells per unit area, for example, per 1 $mm^2$ or per 1 $cm^2$. In some embodiments, the predetermined number may be the number of cells per unit volume, for example, per 1 $mm^3$ or per 1 $cm^3$. For example, the predetermined number may be about 1000 to 100000 per unit area or 100 to 100000 per unit volume.

For the cell remaining substantially stationary in the culture medium, the intensity of light received by the light-receiving portions 42 decreases over time as the cell proliferates two- or three-dimensionally. This allows accurate estimation of the number of cells included in the culture medium. For the cell moving in the culture medium, the probability of the cell included in the portion of the culture medium corresponding to the slit 31 may be measured per unit time, for example, per minute or per hour (presence time per unit time). In another example, the number of cells crossing the portion of the culture medium corresponding to the slit 31 may be measured per unit of time. Based on these measurements, the number of cells included in the culture medium can be estimated accurately.

The intensity of the light emitted from the light source 10 may be controlled to increase over time. After sufficient proliferation of cells, a large number of cells are densely contained in the cell culture vessel. These cells scatter the first vertical light VL1, causing the amount of light to be received by the light-receiving portions 42 (amount of light received) to be small. Thus, when the intensity of light emitted from the light source 10 is constant, determining that the cells have proliferated to the predetermined number or greater tends to be difficult. In other words, the amount of light received by the light-receiving portions 42 may be close to background noise. In this case, the time point (timing) to stop cell culture may be difficult to determine. Controlling the intensity of the emitted light to increase over time as described above slows the decrease in the amount of light received due to an increase in the number of proliferated cells. Thus, the amount of received light is maintained above a certain level when a large number of cells are densely contained in the cell culture vessel after sufficient proliferation, facilitating determination of the time point to stop cell culture. The pattern of a change in the intensity of light emitted from the light source 10 may be designed to be in accordance with the pattern of a change in the amount of received light. For example, the intensity of the light emitted from the light source 10 may be increased linearly when the amount of light received decreases linearly, or the intensity of the light emitted from the light source 10 may be increased nonlinearly (e.g., exponentially) when the amount of light received decreases nonlinearly (e.g., exponentially). For example, $I_0$ may be less than $I_1$ and not more than $10I_0$, but the intensity may not be in this range where $I_0$ is the intensity of the light emitted from the light source 10 at the start of the observation of the cell count, and $I_1$ is the intensity of the light emitted from the light source 10 at the end of the observation of the cell count. The intensity of the emitted light may be kept constant instead of linearly increasing. The signals obtained by receiving light at the light-receiving portions 42 may be amplified to increase the signal intensity. Although this also amplifies background noise, a filter may be used to reduce the background noise.

A light emission intensity controller that performs the control described above may be included in, for example, a control board 90, a monitoring device 91, or a computer system 92 in the sample observation system 101 described later.

The control may also be performed to determine a time point to stop cell culture by inferring the trend of a change in the amount of light received under various conditions. To perform such control, a machine learning model developed with a neural network program (also referred to as a multilayer perceptron program), commonly known as an artificial intelligence (AI) program, may be used. The machine learning model may be a deep learning model. Training data (also referred to as teaching data) for building the machine learning model includes data about the time elapsed during the operation of the light-receiving member 40 and data about the amount of light received in the light-receiving portions 42. For example, the amount of light received may decrease linearly or nonlinearly (e.g., exponentially) with respect to the time elapsed, depending on conditions (parameters) such as the cell type, culture medium type, and temperature. A machine learning model may be used to autonomously derive the laws and rules in changes in the amount of light received in response to various conditions to predict changes in the amount of received light. The machine learning model may further infer the most appropriate time point (timing) to stop cell culture based on various conditions.

More specifically, a system may be designed to notify users by activating an alarm, such as an alarm sound, an alarm lamp, or an alarm message, when the time to stop cell culture is close. Users may also stop cell culture based on data about the actual amount of received light. Cell culture may also be stopped automatically when the time to stop comes. When a vessel 20 that allows concurrent cell culture under multiple different conditions, such as a multi-well plate, is used, cell culture may be automatically stopped well by well by inferring the time point to stop cell culture for each well.

A cell culture stop controller that performs the control described above may be included in, for example, a control board 90, a monitoring device 91, or a computer system 92, in the sample observation system 101 described later.

Cell culture media contain phenol red as a pH indicator, and a medium containing phenol red is colored red in the optimal pH range of 6.8 to 7.2 (neutral) for a cell. However, as the pH decreases during cell culture, the medium has a higher absorption peak at a wavelength of around 430 to 440 nm and a lower absorption peak at a wavelength of around 560 nm. The medium thus turns yellow. The timing for medium replacement can thus be determined by measuring the pH value of the culture medium. In culturing cells in many cell culture vessels, visually observing every vessel to determine the timing for culture medium replacement after sufficient cell proliferation is time-consuming. The sample observation apparatus 100 according to the present embodiment greatly reduces the burden on users.

More specifically, for example, a 0.04 w/v % phenol red solution (FUJIFILM Wako Pure Chemical Corporation, with the molecular formula of $C_{19}H_{14}O_5S$ and the molecular weight of 354.38) may be used. The phenol red solution may be prepared by, for example, adding 14.2 ml of a 0.02 mol/L sodium hydroxide solution and water to 0.10 g of phenol red to obtain 250 ml of a phenol red solution.

In the absorption spectrum of phenol red, the absorption with the green wavelength of 560 nm changes largely when the solution turns acidic. The PIN amorphous silicon photodiode has the highest quantum efficiency at a wavelength of around 560 nm. The use of light-receiving portions 42 including the PIN amorphous silicon photodiode allows a color change to be detected without a color filter or a complicated structure. Light detected by the amorphous silicon photodiode accumulates as an electric charge, for which the amount is then read to detect a color change.

Cell culture typically involves medium replacement or subculturing every 2 to 4 days. Once the cells have undergone sufficient proliferation in the culture vessel, the cells and the culture medium are collected to replace the culture medium or subculture. The collected cells and the culture medium may be used in subsequent experiments.

Sample Observation System

Second Embodiment

The sample observation system 101 according to a second embodiment of the present invention will now be described with reference to the drawings.

Figure 13A:
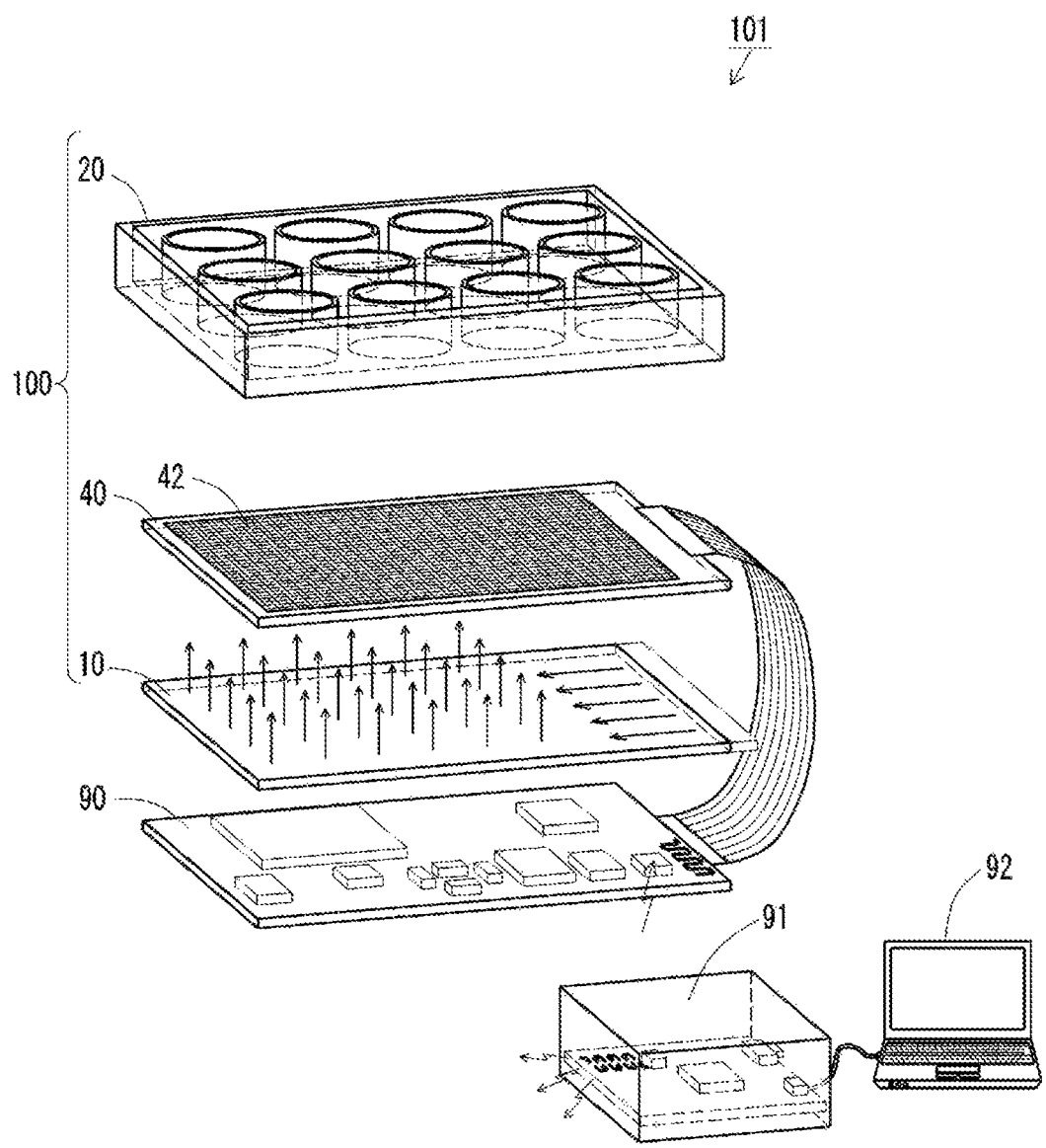
FIG. 13A is an exploded perspective view of a sample observation system according to an embodiment of the present disclosure.
Figure 13B:
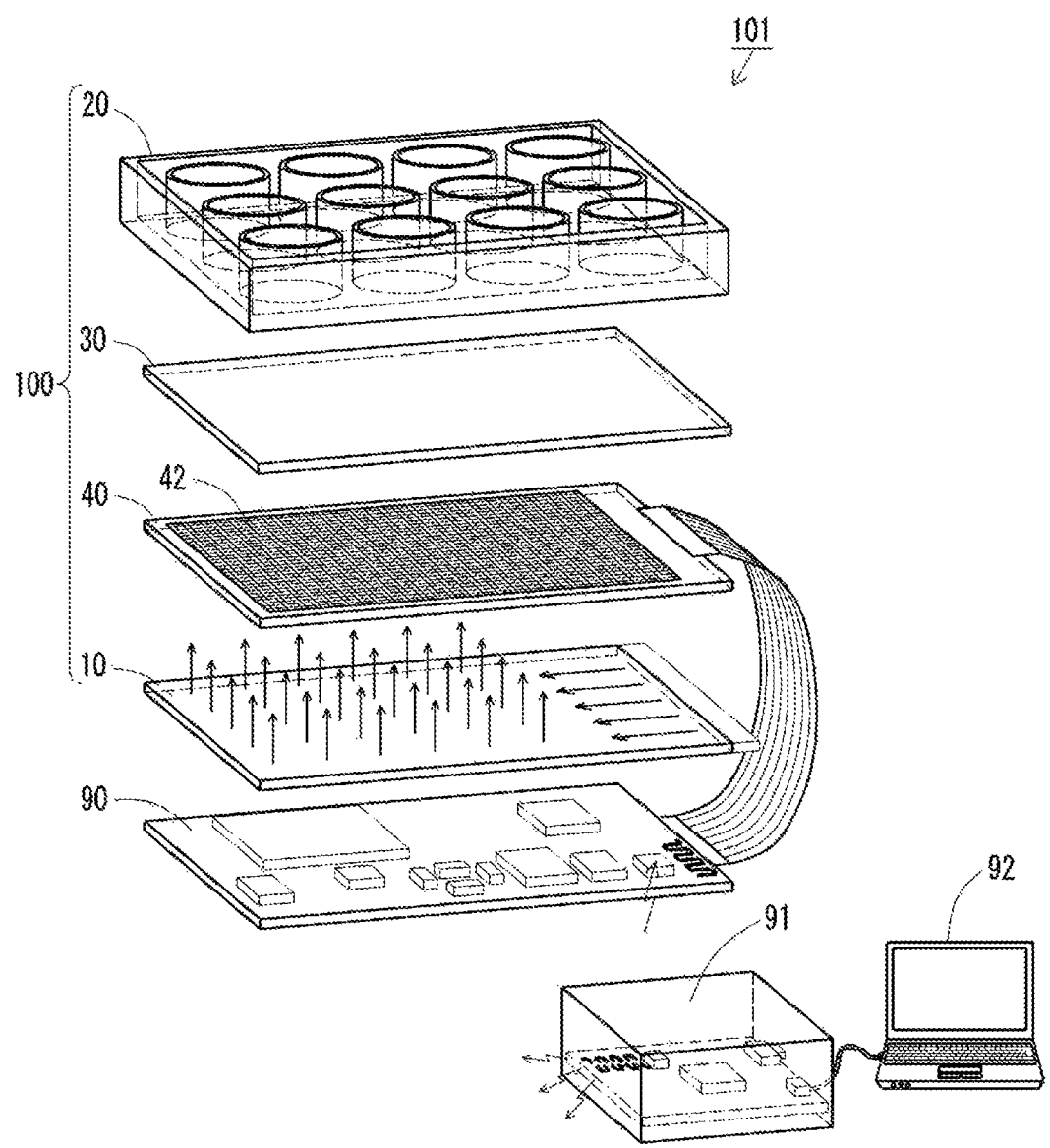
FIG. 13B is an exploded perspective view of a sample observation system according to the embodiment of the present disclosure.

As illustrated in FIGS. 13A and 13B, in the present embodiment, the sample observation system 101 includes a sample observation apparatus 100, a control board 90 as a control device, and a monitoring device 91. The sample observation apparatus 100 is the same or similar as in the first embodiment. The sample observation apparatus 100 in the sample observation system 101 illustrated in FIG. 13A has the structure illustrated in FIG. 1A. The sample observation apparatus 100 in the sample observation system 101 illustrated in FIG. 13B has the structure illustrated in FIG. 1B including a slit member 30. The components corresponding to those in the above embodiment are given the same reference numerals and will not be described repeatedly.

The sample observation apparatus 100 is connected to the control board 90, which is connected to the monitoring device 91. The connection may be achieved with a wire or wirelessly.

The control board 90 transmits data obtained from the light-receiving portions 42 in the light-receiving member 40 to the monitoring device 91. The control board 90 may include a rechargeable battery, a charging control integrated circuit, an impedance matching circuit, an RF reader integrated circuit, a microcomputer, a nonvolatile memory, and a control integrated circuit. The data obtained from the light-receiving portions 42 includes data about the amount of samples 70 and data about the pH value of the medium 80.

The monitoring device 91 receives data transmitted from the control board 90. The monitoring device 91 may include a control integrated circuit, a microcomputer, and a field-programmable gate array (FPGA).

The monitoring device 91 may be connected to the computer system 92 and transmit received data to the computer system 92. The computer system 92 may include a display for displaying the received data.

In a variation of the present embodiment, a sample observation system 101 includes one or more sample observation apparatus 100, one or more control boards 90, and a monitoring device 91. One or more control boards 90 are connected to one or more sample observation apparatuses 100, either to control the operations for sample observation of the sample observation apparatus 100 collectively, or to control the sample observation operations of each of the sample observation apparatuses 100 individually. For example, the monitoring device 91 communicates with each of the control boards 90 and outputs monitoring information about the sample observation apparatuses 100. The data transmitted from the sample observation apparatuses 100 to the corresponding control boards 90 are transmitted from the respective control boards 90 to the single monitoring device 91. The data transmitted to the monitoring device 91 may be transmitted further to the computer system 92. This greatly reduces the time used for obtaining data from the sample observation apparatuses 100, thus allowing more efficient observation of many samples 70. In this case, each of the sample observation apparatuses 100 may include the same sample 70 and the same medium 80, or the same sample 70 and a different medium 80, a different sample 70 and the same medium 80, or a different sample 70 and a different medium 80. These allow tests on different samples and different media to be performed at the same time.

In a variation of the present embodiment, as illustrated in FIG. 14, second illumination light IL2 from a light source 10 included in a sample observation apparatus 100 may illuminate a portion of the vessel 20 alone. For the vessel 20 including multiple vessel sections, the light source 10 may emit second illumination light IL2 toward, for example, vessel sections individually. In FIG. 14, the part of the light source 10 that emits the second illumination light IL2 and the corresponding vessel section are enclosed in rounded squares. The second illumination light IL2 may illuminate any number of vessel sections at a time, and may also illuminate one vessel section at a time after another. The medium 80 and the samples 70 in the vessel sections may be the same or different from one another.

As illustrated in FIG. 15, the light source 10 may also emit the second illumination light IL2 toward a set of multiple vessel sections. In FIG. 15, the part of the light source 10 that emits the second illumination light IL2 and the corresponding vessel section are enclosed in rounded rectangles. The set of multiple vessel sections may include, for example, vessel sections in a longitudinal row, vessel sections in two crosswise rows, vessel sections in two longitudinal rows, or a combination of these. The light source 10 may illuminate one set of multiple vessel sections after another, or may illuminate individual vessel sections and sets of multiple vessel sections in a predetermined sequence. The sequence of illumination can be defined as appropriate for the types and quantities of the media 80 and samples 70. The entire vessel 20 not being illuminated at once reduces the peak power consumption of the light source 10.

Although embodiments of the present disclosure have been described in detail, the present disclosure is not limited to the embodiments described above, and may be changed or varied in various manners without departing from the spirit and scope of the present disclosure. The components described in the above embodiments may be entirely or partially combined as appropriate unless any contradiction arises.

The present disclosure may be embodied in various forms without departing from the spirit or the main features of the present disclosure. The embodiments described above are thus merely illustrative in all respects. The scope of the present invention is defined not by the description given above but by the claims. Any variation and alterations contained in claims fall within the scope of the present invention.

REFERENCE SIGNS

10 light source
20 vessel
21 attachment
30 slit member
31 slit
32 light shield
40 light-receiving member
41 light-transmissive portion
42 light-receiving portion
43 light-receiving portion unit
44 light-shielding member
50 reflector
60 lid
70 sample
80 medium
90 control board
91 monitoring device
100 sample observation apparatus
101 sample observation system

The invention claimed is:

1. A sample observation apparatus, comprising:
   a transparent vessel configured to accommodate a medium containing a sample;
   a light source below the vessel, the light source being configured to emit illumination light toward an inside of the vessel;
   a light-receiving member configured to receive scattered light being the illumination light scattered by the medium, the light-receiving member including a light-transmissive portion and a plurality of light-receiving portions and being located between the medium and the light source and overlapping the light source; and
   a slit to allow the scattering light to travel through, the slit being located between the medium and the light-receiving member,
   the slit including a plurality of slits,
   the plurality of light-receiving portions each overlapping a corresponding slit of the plurality of slits as viewed in plan.

2. The sample observation apparatus according to claim 1, wherein
   the light-receiving member includes a light-shielding member facing the light source.

3. The sample observation apparatus according to claim 1, further comprising:
   a reflector facing the light source with the vessel between the light source and the reflector.

4. The sample observation apparatus according to claim 1, further comprising:
   an attachment to allow the vessel to be detached from and attached to the light source.

5. The sample observation apparatus according to claim 1, wherein
   the light-relieving member is located in the vessel on a bottom surface of the vessel, and
   the slit is located immediately above the light-receiving member.

6. The sample observation apparatus according to claim 1, wherein
   the light-relieving member is located between the light source and the vessel, and the slit is located in the vessel on a bottom surface of the vessel.

7. The sample observation apparatus according to claim 1, wherein
the light-relieving member is located between the light source and the vessel,
the slit is located between the light-relieving member and the vessel, and
the vessel, the slit, the light-receiving member, and the light source are in close contact with one another.

8. The sample observation apparatus according to claim 1, wherein
the plurality of light-relieving portions has a square shape in a plan view, and
the light-transmissive portion has an area larger than a total area of the plurality of light-receiving portions.

9. The sample observation apparatus according to claim 1, wherein
the plurality of light-relieving portions has a rectangular frame shape in a plan view.

10. The sample observation apparatus according to claim 1, wherein
the light-receiving member includes a light-transmissive portion and a plurality of light-receiving portion units, and
each of the plurality of light-receiving portion units includes light-transmissive portions arranged in a grid in a plan view and the plurality of light-receiving portions square-shaped in plan a view, and the plurality of light-receiving portions are separated by the grid of light-transmissive portions.

11. The sample observation apparatus according to claim 1, wherein
the light source is controllable to emit light with an intensity increasing over time.

12. The sample observation apparatus according to claim 1, wherein
the light source emits the illumination light to a portion of the vessel.

13. The sample observation apparatus according to claim 12, wherein
the vessel includes a plurality of target areas for illumination, and
the light source illuminates the plurality of target areas individually.

14. The sample observation apparatus according to claim 1, wherein
the slit includes a light shield.

15. The sample observation apparatus according to claim 1, wherein
the sample is a cell, and the medium is a cell culture medium.

16. The sample observation apparatus according to claim 15, wherein
the cell is an induced pluripotent stem cell or a mesenchymal stem cell.

17. The sample observation apparatus according to claim 15, wherein
the light-receiving member obtains a signal to measure a pH value of the cell culture medium based on transmittance of the scattered light in the cell culture medium.

* * * * *